United States Patent
Clarke et al.

(10) Patent No.: US 6,248,264 B1
(45) Date of Patent: Jun. 19, 2001

(54) NEUTRAL COLORING PHOTOCHROMIC 2H-NAPHTHO[1,2-B] PYRANS AND HETEROCYCLIC PYRANS

(75) Inventors: David A. Clarke, Brighouse; Bernard Mark Heron, Yorkshire; Christopher David Gabbutt; John David Hepworth, both of Lancashire; Steven Michael Partington; Stephen Nigel Corns, both of Huddersfield, all of (GB)

(73) Assignee: James Robinson Limited, Huddersfield (GB)

( * ) Notice: Subject to any disclaimer, the term of this patent is extended or adjusted under 35 U.S.C. 154(b) by 0 days.

(21) Appl. No.: 09/381,809

(22) PCT Filed: Mar. 25, 1998

(86) PCT No.: PCT/GB98/00904

§ 371 Date: Nov. 1, 1999

§ 102(e) Date: Nov. 1, 1999

(87) PCT Pub. No.: WO98/42693

PCT Pub. Date: Oct. 1, 1998

(30) Foreign Application Priority Data

Mar. 25, 1997 (GB) .................................................. 9706202

(51) Int. Cl.⁷ ........................... G02B 5/23; C07D 311/92
(52) U.S. Cl. ........................... 252/586; 549/389; 549/58; 549/60; 544/150; 546/196; 546/282.7; 548/465; 548/525; 351/163
(58) Field of Search ............................ 252/586; 549/389, 549/58, 60; 544/150; 546/196, 282.7; 548/465, 525; 351/163

(56) References Cited

U.S. PATENT DOCUMENTS

| 4,818,096 | 4/1989 | Heller et al. . |
|---|---|---|
| 4,990,287 | 2/1991 | Bennion et al. . |
| 5,458,814 | 10/1995 | Kumar et al. . |
| 5,623,005 | * 4/1997 | Rickwood et al. .................. 252/586 |
| 6,022,496 | * 2/2000 | Kawabata et al. .................. 252/586 |
| 6,080,338 | * 6/2000 | Kumar ................................. 252/586 |

FOREIGN PATENT DOCUMENTS

| 8295690 | 11/1996 | (JP) . |
|---|---|---|
| 9420869 | 9/1994 | (WO) . |
| 9604576 | 2/1996 | (WO) . |
| 9721698 | 6/1997 | (WO) . |

OTHER PUBLICATIONS

Patent Abstracts of Japan, vol. 97, No. 3, Mar. 31, 1997.
Research Disclosure, vol. 361, No. 36144, May 1994, pp. 266–268.

* cited by examiner

*Primary Examiner*—Philip Tucker
(74) *Attorney, Agent, or Firm*—Stevens, Davis, Miller & Mosher, L.L.P.

(57) ABSTRACT

Compositions comprising a naphtho [1,2-b]pyran of formula (I):

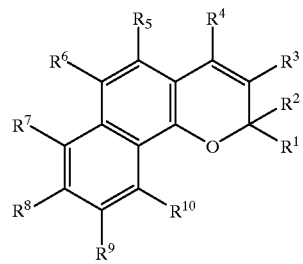

wherein $R^7$ and/or $R^9$ is hydrogen or an amino group provided that $R^7$ and $R^9$ are not both hydrogen, and the other substituents are as defined in the specifcation.

10 Claims, No Drawings

NEUTRAL COLORING PHOTOCHROMIC 2H-NAPHTHO[1,2-B] PYRANS AND HETEROCYCLIC PYRANS

The present invention relates to certain new photochromic pyran derivatives and to their use.

Photochromism is a well-known physical phenomenon which is observed with certain classes of chemical compounds. A detailed discussion of this phenomenon can be found in "Photochromism: Molecules and Systems," Studies in Organic Chemistry 40, Eds. H Dürr and H. Bouas-Laurent, Elsevier, 1990.

The 2H-naphtho[1,2-b]pyran system is known to be capable of exerting a photochromic effect as described, for example, U.S. Pat. No. 3,567,605 and U.S. Pat. No. 4,826,977. U.S. Pat. No. 3,567,605 provides an example of a 2H-naphtho[1,2-b]pyran which remains coloured at ambient temperatures for several hours, and U.S. Pat. No. 4,826,977 describes a series of yellow/orange colouring 2H-naphtho[1,2-b]pyrans containing a spiro-adamantane group at the 2-position, amongst other 2H-[1]benzopyran and isomeric naphthopyran systems.n The basic structural unit of the 2H-naphtho[1,2-b]pyran system, in this instance substituted at C-2 with a spiro-adamantane group, is illustrated below.

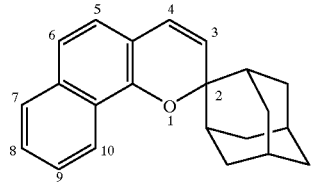

A range of purple/blue colouring 2(4-aminophenyl)-2-alkyl-2H-naphtho[1,2-b]pyrans have also been described in U.S. Pat. No. 4,818,096.

A series of photochromic 2H-naphtho[1,2-b]pyrans, amongst other 2H-[1]benzopyrans and isomeric naphthopyrans, bearing a cyclopropyl group as one of the substituents at the 2-position is described in article WO92/01959. It is also commented that the compound 2-cyclopropyl-2-p-methoxyphenyl-5-methyl-2H-naphthop[1,2-b]pyran and several other analogues are of particular current interest, but no reasons were presented either to substantiate such interest or on any significance of the 5-methyl group.

It is stated in U.S. Pat. No. 5,066,818 (1991) that "The compound, 2,2diphenyl-2H-naphtho[1,2-b]pyran, also colours on exposure to near ultraviolet light at room temperature but does not bleach in a reasonable period of time. Substitution of the phenyl substituents in the meta and para positions have little effect on the rate of bleaching of these compounds."

The very high optical density of 2,2-diaryl-2H-naphtho[1,2-b]pyrans achieved under irradiation and their slow attendant fade (bleaching) on removal of the source of irradiation relative to the photochromic properties displayed by the isomeric 3,3-diaryl-3H-naphtho[2,1-b]pyrans has been recently noted by B. van Gemert et al. (*Mol. Cryst. Liq. Cryst.*, 1994, 246, 67). The relatively slow attendant fade of the 2,2-diaryl-2H-naphtho[1,2-b]pyrans was rationalised by the absence of steric crowding in the ring opened (coloured) quinoidal/zwitterionic forms. Such steric crowding is thought to be present for the ring opened form of the 3,3-diaryl-3H-naphtho[2,1-b]pyrans and accounts for their relatively rapid fade.

Pilkington Brothers Limited have also commented on the fading of photochromic materials in Research Disclosure.

Two structurally similar deep colouring photochromic 2,2-diaryl-2H-naphtho[1,2-b]pyrans, namely 2,2-bis(4-methoxyphenyl)-5,6-dimethyl-2H-naphtho[1,2-b ]pyran and 2-(4-methoxyphenyl)-2-(4-trifluoromethylphenyl)-5,6-dimethyl-2H-naphtho-[1,2-b]pyran are described, which exhibit markedly improved attendant fade compared with the non-methyl substituted analogues. These improved rates of fade are attributed to the combined presence of methyl groups at the 5- and 6-positions, which are said to exert steric pressures upon the ring opened (coloured) quinoidal/zwitterionic forms, thereby enhancing the ring closure to the uncoloured naphthopyran system. However, these fast fade materials described by Pilkington plc with substituents at both the 5- and 6-positions are difficult to make, requiring a long multi-stage process which renders them unattractive commercially. Thus the use of two substituents at the 5- and 6-positions to achieve rapid fade in these 2,2-diaryl compounds has the disadvantage of manufacture complexities.

Two recent U.S. Pat. Nos., 5,458,814 and 5,514,817 describe the synthesis of a range fast fading intense yellow to red/purple colouring 2,2-diaryl-2H-naphtho[1,2-b]pyrans and phenanthropyrans which either possess a 5-substituent or are 5,6-disubstituted.

We have investigated these known photochromic compounds and have found that, for intense colour generation, compounds having 2,2-diaryl substituents are preferred. Also the presence of a 5 substituent in these 2,2-diaryl-2H-naphtho[1,2-b]pyrans ensures rapid fading of the colour generated upon irradiation. Furthermore, we have found that brown and brown/red photochromic 2,2-diaryl-2H-naphtho[1,2-b]pyrans can be obtained when the said 2,2-diaryl-2H-naphtho[1,2-b]pyran is substituted in the 7- or 9-position with an amino function.

According to the present invention, there is provided a polymeric host material or a solution including a photochromic compound of the formula I

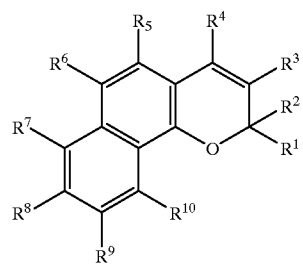

(I)

In graphic formula I above, $R^1$ and $R^2$ are each selected from unsubstituted, mono-, di- or polysubstituted aryl groups, phenyl and heteroaryl groups, preferably mono- or di-substituted phenyl wherein the or each aryl group is not a naphthyl group. When $R^1$ and/or $R^2$ is selected from heteroaryl groups, each may be thienyl, benzo[b]thienyl, furyl, benzo[b]furyl, pyrryl, indolyl, pyridyl, quinolyl, isoquinolyl, pyrimidyl, oxazolyl, isoxazolyl, thiazolyl, isothiazolyl, pyrazolyl, imidazolyl or benzimidazolyl.

The substituents for the aryl, naphthyl and heteroaryl groups representing $R^1$ and $R^2$ are linear or branched $C_1$–$C_{20}$ alkyl, $C_1$–$C_{20}$ cycloalkyl, $C_1$–$C_{20}$ bicycloalkyl, $C_1$–$C_{20}$ polycycloalkyl, linear or branched $C_1$–$C_{10}$ haloalkyl, linear or branched $C_1$–$C_{10}$ perhaloalkyl, linear or branched $C_1$–$C_{10}$ perhaloalkenyl, linear or branched $C_1$–$C_{10}$ alkenyl, $C_1$–$C_{10}$ alkynyl, linear or branched $C_1$–$C_{10}$ alkoxy, linear or branched $C_1$–$C_{10}$ alkylthio, linear or branched $C_1$–$C_{10}$ alkoxy (linear or branched $C_1$–$C_{10}$alkyl), linear or branched $C_1$–$C_{10}$ hydroxyalkyl, linear or branched $C_1$–$C_{10}$ aminoalkyl, aryl, phenyl, heteroaryl, halogen, nitrile, nitro, amino, linear or branched $C_1$–$C_{20}$ alkoxycarbonyl, hydroxyl, formyl, acetyl, amido, $C_1$–$C_5$ alkyl amido, $C_1$–$C_5$ dialkylamido, aroyl, benzoyl, alkyl $C_1$–$C_5$ amino, dialkyl $C_1$–$C_5$ amino, arylamino, diarylamino, aryl $C_1$–$C_5$ alkylamino and cyclicamino groups arylsulfinyl, arylsulfanyl, arylsulfonyl, linear or branched $C_1$–$C_{10}$ alkylsulfonyl, P(O)(O—$C_1$–$C_{10}$ alkyl)$_2$.

For example, the substituents for the aryl and heteroaryl groups representing $R^1$ and $R^2$ may be $C_1$–$C_5$ alkyl, $C_1$–$C_5$ haloalkyl, $C_1$–$C_5$ alkoxy, $C_1$–$C_5$ alkoxy($C_1$–$C_5$)alkyl, amino-$C_1$–$C_5$ alkyl, hydroxy-$C_1$–$C_5$ alkyl, halogen, amino, alkyl $C_1$–$C_5$ amino, dialkyl $C_1$–$C_5$ amino and cyclic amino groups (for example, aziridino, pyrrolidino, piperidino, morpholino, thiomorpholino, indolino, piperazino, $C_1$–$C_5$ N-alkylpiperazino N-arylpiperazino). Other heteroaryl groups of $R^1$ and $R^2$ may be triazolyl, benzotriazolyl, or tetrazolyl.

Phenyl, aryl and heteroaryl ring substituents may be located at the o-, m- or p-positions. Typically, each phenyl group contains less than 3 substituents.

$R^3$ and $R^4$ are each hydrogen, $R^1$, $R^2$ or as defined for $R^5$ below.

$R^5$ may be selected from linear or branched $C_1$–$C_{10}$ alkyl, $C_1$–$C_{20}$ cycloalkyl, $C_1$–$C_{20}$ bicycloalkyl, $C_1$–$C_{20}$ polycycloalkyl, linear or branched $C_1$–$C_{10}$ haloalkyl, linear or branched $C_1$–$C_{10}$ perhaloalkyl, linear or branched $C_1$–$C_{10}$ perhaloalkenyl, linear or branched $C_1$–$C_{10}$ alkenyl, $C_1$–$C_{10}$ alkynyl, linear or branched $C_1$–$C_{10}$ alkoxy, linear or branched $C_1$–$C_{10}$ alkylthio, linear or branched $C_1$–$C_{10}$ alkoxy (linear or branched $C_1$–$C_{10}$ alkyl), linear or branched $C_1$–$C_{10}$ hydroxyalkyl, linear or branched $C_1$–$C_{10}$ aminoalkyl, aryl, phenyl, heteroaryl, halogen, nitrile, nitro, amino, linear or branched $C_1$–$C_{20}$ alkoxycarbonyl, hydroxyl, formyl, acetyl, amido, $C_1$–$C_5$ alkyl amido, $C_1$–$C_5$ dialkylamido, aroyl, benzoyl, alkyl $C_1$–$C_5$ amino, dialkyl $C_1$–$C_5$ amino, arylamino, diarylamino, aryl $C_1$–$C_5$ alkylamino and cyclicamino groups, arylsulfinyl, arylsulfanyl, arylsulfonyl, or linear or branched $C_1$–$C_{10}$ alkylsulfonyl, P(O)(O—$C_1$–$C_{10}$ alkyl)$_2$. For example, $R^5$ may be selected from $C_1$–$C_{10}$ alkyl, $C_1$–$C_{10}$ haloalkyl, $C_1$–$C_{10}$ perfluoroalkyl, $C_1$–$C_5$ perfluoroalkenyl, $C_1$–$C_5$ alkenyl, $C_1$–$C_5$ alkynyl, $C_1$–$C_{10}$alkoxy, $C_1$–$C_{10}$ perfluoroalkoxy, $C_1$–$C_5$ alkoxy($C_1$–$C_5$) alkyl, $C_1$–$C_5$ hydroxyalkyl, halogen, nitrile, nitro, amino, $C_1$–$C_5$ alkylamino, $C_1$–$C_5$ dialkylamino, cyclic amino (for example, aziridino, pyrrolidino, piperidino, morpholino, thiomorpholino, indolino, piperazino, $C_1$–$C_5$N-alkyl-piperazino N-arylpiperazino), arylamino, diarylamino, aryl $C_1$–$C_5$ alkylamino, $C_1$–$C_5$ oxoalkyl, phenyl, aryl, substituted aryl, naphthyl, substituted naphthyl, aroyl, substituted aroyl, formyl, carboxyl, $C_1$–$C_{20}$ alkoxycarbonyl, $C_1$–$C_5$ haloalkyloxycarbonyl, aryloxylcarbonyl, substituted aryloxylcarbonyl.

$R^5$ may also be selected from the alkenyl function illustrated immediately below:

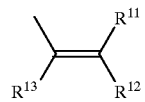

Where $R^{11}$ and/or $R^{12}$ and/or $R^{13}$ will each be selected from hydrogen or those substituents specified above for $R^5$ in formula I. In addition to these substituents $R^{11}$ and $R^{12}$ and $R^{13}$ may be selected from H, CN, NO$_2$, CHO, $C_1$–$C_5$ alkoxycarbonyl, benzoyl, and phenylsulfonyl.

In graphic formula I $R^6$ and $R^8$ and $R^{10}$ may be selected from hydrogen, in addition to those groups specified for $R^1$, $R^2$ and $R^5$ above.

To impart a brown or brown/red colour in the darkened state $R^9$ and or $R^7$ are selected from amino, substituted amino including alkyl $C^1$–$C_5$ amino, dialkyl $C_1$–$_{C5}$ amino, arylamino, aryl alkyl $C_1$–$C_5$ amino, diarylamino and cyclic amino groups (for example, aziridino, pyrrolidino, piperidino, morpholino, thiomorpholino, indolino, piperazino, $C_1$–$C_5$ N-alkylpiperazino), this selection is illustrative and not limiting.

Typically, though not always, two or three groups selected from $R^7$, $R^8$, $R^9$ and $R^{10}$ are hydrogen though at least one of $R^7$ and $R^9$ will be an amino function.

The photochromic properties exhibited by the novel pyran compounds of the present invention, namely those of high induced optical density and rapid bleaching of the brown, red/brown coloured form, render these compounds particularly useful as photochromic materials for incorporation into polymeric host materials so as to impart photochromic properties to the said polymeric host materials. Examples of applications of the polymeric host materials containing photochromic materials of the present invention include the manufacture of lenses for sunglasses and ophthalmic lenses, optical filters and windows for vehicles such as cars (including sunroofs), aircraft and ships and architectural uses e.g. windows for homes and for photochromic 'stained glass' windows.

The photochromic pyrans of the present invention are incorporated into the 'plastic' host material by well established protocols for example as described in European patent no. 0254020 or U.S. Pat. No. 5,066,818.

The high induced optical density of the photochromic compounds of the present invention enables the amount of the photochromic material required so as to impart a useful degree of photochromism to a polymeric host material or to a solution to be greatly reduced, thereby enabling a considerable saving of synthetic effort and cost. Furthermore, the use of reduced quantities of the photochromic materials of the present invention has the bonus that there is a consequent reduction in any undesirable colour that the photochromic materials may impart in the bleached state, either by way of inherent colour of the material itself or by the formation of coloured fatigue/degradation products through use of the photochromic material.

Typical host materials are optically clear polymer materials, such as polymers of polyol (allyl carbonate)-monomers, polyacrylates such as polymethylmethacrylates, cellulose acetate, cellulose triacetate, cellulose acetate propionate, cellulose acetate butyrate, poly(vinyl acetate), poly(vinyl alcohol), polyurethanes, polycarbonate, polyethylene terephthalate, polystyrene, poly(triethyleneglycol dimethylacrylate), poly(diethyleneglycol bis(allyl carbonate)) and various copolymer mixes.

The pyran compounds of the present invention may be prepared by a general method which is based on the following reaction scheme:

Scheme

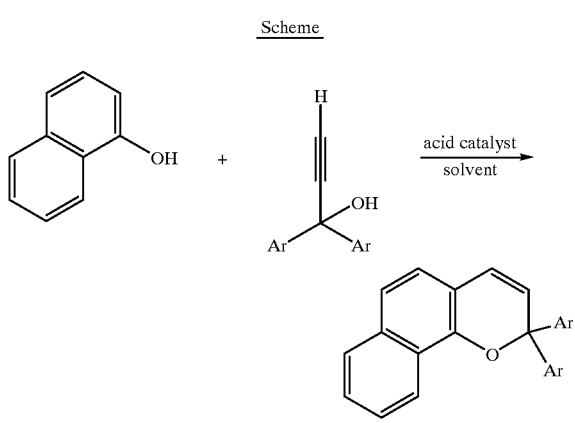

This general synthetic methodology has been descibed in detail, for example, by L. Merlini in 'Advances in Heterocyclic Chemistry,' 1975, vol. 18, page 159, and by R. Guglielmetti in "Photochromism: Molecules and Systems," Studies in Organic Chemistry 40, chp. 8, Eds. H Dürr and H. Bouas-Laurent, Elsevier, 1990, and also in several patent documents, for example, U.S. Pat. No. 5,066,818; U.S. Pat. No. 4,990,287, WO 92/09593 and WO95/05382. The synthesis of the propargyl alcohols shown in the scheme above are obtained in a known manner, for example, T. F. Rutledge in 'Acetylenic Compounds,' Reinhold, N.Y., 1968. The 1-naphthols and related hydroxy compounds are either commercially available or obtained by known synthetic methods, or derived from such methods. Some of the 1-naphthols and related hydroxy compounds or precursors thereof have been described in the chemical literature, for example, ethyl 1-acetoxydibenzo thiophene-3-carboxylate see (S. Gronowitz et al., Acta. Pharm. Suec., 1978, 15, 337) and 3-hydroxypropyl-1-naphthol see (R. F. Frank et al., J. Chem. Soc., Chem. Commun., 1984, 761). The use of the Stobbe condensation to prepare 1-naphthols has also been discussed (see Organic Reactions 1951, 6,1).

The acid catalyst may be selected from acidic alumina (Brockmann 1), acetic acid; trifluoroacetic acid, silica, clays (e.g. montmorillionite, tonsil) or acidic exchange resins. Organic solvents frequently employed for the reaction include benzene, toluene, xylene and relatively high boiling alkanes.

The following examples illustrate but do not limit the invention:

EXAMPLE 1

Methyl 2,2-bis(4-methoxyphenyl)-9-morpholino-2H-naphtho [1,2-b]pyran-5-carboxylate (a) Ethyl 4-acetoxy4—morpholino-2-naphthoate.

A solution of 4-morpholinobenzaldehyde (11 g, 57.5 mmol) and diethyl succinate (15.03 g, 86.3 mmol) in anhydrous ethanol (50 cm³) was added dropwise over 45 minutes to a vigorously stirred warm ~40–50° C., solution of sodium ethoxide (from sodium 2.64 g, 115 mmol) in anhydrous ethanol (250 cm³) under $N_2$. On completion of the addition the solution was refluxed for 4 hours and then cooled to room temperature.

The reaction mixture was reduced to ~⅕ of the original volume and the resulting viscous oil was diluted with water (500 cm³), cautiously neutralised with HCl (2M) and the resulting two phase mixture extracted with ethyl acetate (5×50 cm³). The combined EtOAc solutions were extracted with aq. sat. $NaHCO_3$ solution (5×75 cm³). The combined aq. $NaHCO_3$ solutions were cautiously neutralised with HCl (2M) and the resulting two phase mixture extracted with EtOAc (4×75 cm³). The combined EtOAc extracts were dried ($Na_2SO_4$) and evaporated to afford a red/brown solid.

A solution of the aforegoing red/brown solid and anhydrous sodium acetate (4.72 g, 57.5 mmol) in acetic anhydride (100 cm³) was refluxed for 3 hours. The solution was cooled to room temperature and then diluted with water (1200 cm³) and allowed to stir for 1.5 hours. The resulting pale brown solid was collected by vacuum filtration, washed well with water (~300 cm³) and air dried.

The solid was recrystallised from EtOAc/hexane and Norit (activated charcoal) to give ethyl 4-acetoxy-6-morpholino-2-naphthoate (yield 14.6 g, theoretical yield= 19.75 g, 73.9%, m.p.=135–137° C. (uncorrected)).

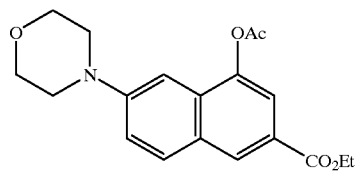

(b) Methyl 4-hydroxy-6-morpholino-2-naphthoate.

A solution of ethyl 4-acetoxy-6-morpholino-2-naphthoate (12.0 g, 34.9 mmol) and sodium hydroxide (8.4 g, 210 mmol) in water (200 cm³) and ethanol (40 cm³) was maintained at 80–90° C. for 3 hours. The cooled solution was poured into water (750 cm³) and cautiously neutralised with HCl (2M). The resulting suspension was extracted with EtOAc.(5×100 cm³). The combined extracts were dried ($Na_2SO_4$) and evaporated to give a brown solid. This solid was dissolved in methanol (200 cm³) containing c. $H_2SO_4$ (~3 cm³) and was refluxed for 5 hours. The cooled mixture was diluted with water (900 cm³) and aq. sat. $NaHCO_3$ solution (100 cm³) then extracted with EtOAc (6×50 cm³). The combined extracts were washed with aq. sat. $NaHCO_3$ (4×100 cm³) and water (100 cm³). Removal of the dried ($Na_2SO_4$) EtOAc gave a pale brown solid which was recrystallised from EtOAc/hexane to afford methyl 4-hydroxy-6-morpholino-2-naphthoate (yield=5.14 g, theoretical yield= 10.0 g, 51.2%, m.p.=231–233.5° C. (uncorrected)).

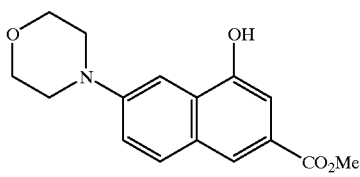

(c) Methyl 2,2-bis(4-methoxyphenyl)-9-morpholino-2H-naphtho[1,2-b]pyran-5-carboxylate.

A solution of methyl 4-hydroxy-6-morpholino-2-naphthoate (1.0 g, 3.5 mmol) and 1,1-di(4-methoxyphenyl) prop-2-yn-1-ol (0.94 g, 3.5 mmol) in toluene (45 cm³) containing acidic alumina (Brockmann 1), (5.0 g) was refluxed for 100 minutes. The cooled solution was filtered and the alumina was washed well with EtOAc (200 cm³). The organic filtrate was washed with aqueous sodium hydroxide (2M, 2×50 cm³) and water (100 cm³). Removal of the dried ($Na_2SO_4$) EtOAc gave an oil which was flash chromatographed over silica using 35% EtOAc in hexane as the eluent to afford a pale yellow solid. Recrystallisation from EtOAc/hexane gave methyl 2,2-bis(4-methoxyphenyl)-9-morpholino-2H-naphtho [1,2-b]pyran-5- carboxylate (yield=0.28 g, theoretical yield=1.87 g 15%, m.p.=153.5–155° C. (uncorrected)).

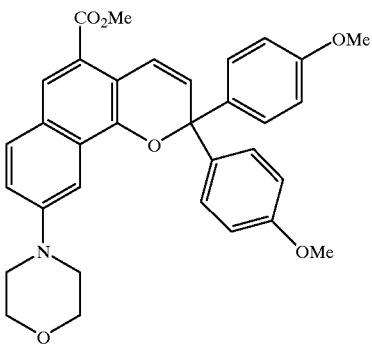

EXAMPLE 2

Methyl 2,2-bis(4-methoxyphenyl)-9-pyrrolidino-2H-naphtho [1,2-b]pyran-5-carboxylate, m.p.=193–194° C. (uncorrected). This compound was obtained by a similar protocol to example 1 above starting from 4pyrrolidinobenzaldehyde.

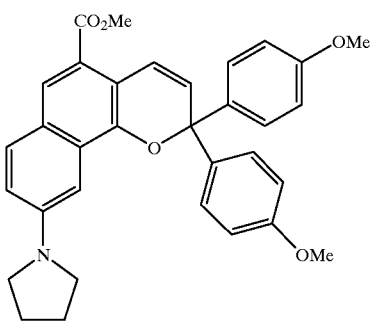

EXAMPLE 3

Methyl 2,2-bis(4-methoxyphenyl)-9-dimethylamino-2H-naphtho [1,2-b]pyran-5-carboxylate, m.p.=168–169° C. (uncorrected). This compound was obtained by a similar protocol to example 1 above starting from 4-dimethylamino-benzaldehyde.

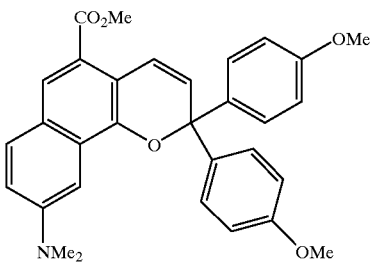

EXAMPLE 4

Methyl 11,11-di(4-methoxyphenyl)-2-methyl-11H-pyrano[2,3-b]carbazole-8-carboxylate.

(a) Ethyl 1-acetoxy-9-methylcarbazole-3-carboxylate.

A solution of 1-methylindole-3-carboxaldehyde (10.17 g, 63.9 mmol) and diethyl succinate (11.7 g, 67.1 mmol) in anhydrous ethanol (50 cm$^3$) was added dropwise over 45 minutes to a vigorously stirred warm ~40–50° C., solution of sodium ethoxide (from sodium 2.93 g, 128 mmol) in anhydrous ethanol (300 cm$^3$) under N$_2$. On completion of the addition the solution was refluxed for 48 hours and then left to stand at RT for 64 hours.

The reaction mixture was reduced to ~⅕ of the original volume and the resulting viscous oil was diluted with water (700 cm$^3$), cautiously acidified with c. HCl and the resulting two phase mixture extracted with ethyl acetate (5×100 cm$^3$). The combined EtOAc extracts were washed with water (100 cm3), dried (Na$_2$SO$_4$) and evaporated to afford a sticky orange solid.

A solution of the aforegoing solid and anhydrous sodium acetate (5.24 g, 63.9 mmol) in acetic anhydride (90 cm$^3$) was refluxed for 3 hours. The solution was cooled to room temperature and then diluted with water (1500 cm$^3$) and allowed to stir for 1.5 hours. The resulting pale brown solid was collected by vacuum filtration, washed well with water (~500 cm$^3$) and air dried.

The solid was recrystallised from EtOAc/hexane and Norit (activated charcoal) to give ethyl 1-acetoxy-9-methylcarbazole-3-carboxylate (yield=6.2 g, theoretical yield=19.9 g, 32.6%, m.p.=123–125° C. (uncorrected)).

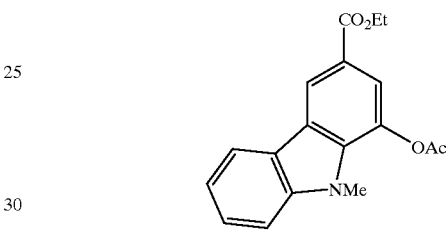

(b) Methyl 1-hydroxy-9-methylcarbazole-3-carboxylate.

A solution of ethyl 1-acetoxy-9-methylcarbazole-3-carboxylate (5.43 g, 17 mmol) and sodium hydroxide (3.48 g, 87 mmol) in water (150 cm$^3$) and ethanol (40 cm$^3$) was maintained at 80–90° C. for 3 hours. The cooled solution was poured into water (400 cm$^3$) and cautiously acidified with c. HCl. The resulting suspension was extracted with EtOAc (5×75 cm$^3$). The combined extracts were dried (Na$_2$SO$_4$) and evaporated to give an orange/brown solid. This solid was dissolved in methanol (100 cm$^3$) containing c. H$_2$SO$_4$ (~1 cm$^3$) and was refluxed for 4 hours. The cooled mixture was diluted with water (500 cm$^3$) and extracted with EtOAc (4×50 cm$^3$). The combined extracts were washed with aq. sat. NaHCO$_3$ (2×100 cm$^3$) and water (100 cm$^3$). Removal of the dried (Na$_2$SO$_4$) EtOAc gave an orange brown solid which was recrystallised from EtOAc/hexane to afford methyl 1-hydroxy-9-methylcarbazole-3-carboxylate (yield=3.37 g, theoretical yield=4.45 g, 75.7%, m.p.=204–206.5° C. (uncorrected)).

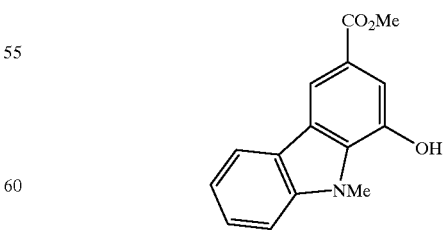

(c) Methyl 11,11-di(4-methoxyphenyl)-2-methyl-11H-pyrano[2,3-b]carbazole8-carboxylate.

A solution of methyl 1-hydroxy-9-methylcarbazole-3-carboxylate (1.0 g, 3.9 mmol) and 1,1-di(4-methoxyphenyl)

prop-2-yn-1-ol (1.05 g, 3.9 mmol) in toluene (45 cm³) containing acidic alumina (Brockmann 1), (4.0 g) was refluxed for 35 minutes. The cooled solution was filtered and the alumina was washed well with EtOAc (200 cm³). The organic filtrate was washed with aqueous sodium hydroxide (2M, 2×50 cm³) and water (100 cm³). Removal of the dried (Na$_2$SO$_4$) EtOAc gave an oil which was flash chromatographed over silica using 25% EtOAc in hexane as the eluent to afford a pale orange solid. Recrystallisation from EtOAc/hexane gave methyl 11,11-di(4-methoxyphenyl)-2-methyl-11H-pyrano[2,3-b]carbazole8-carboxylate (yield=1.10 g, theoretical yield=1.98 g 55.5%, m.p.=185.5–188.0° C. (uncorrected)).

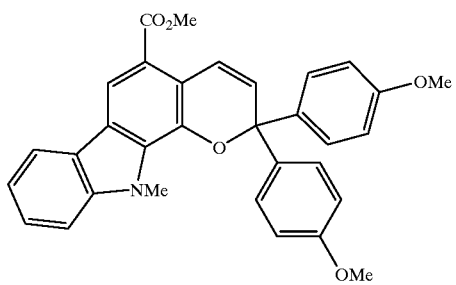

COMPARATIVE EXAMPLE 1

Methyl 9-methoxy-2,2-bis(4-methoxyphenyl)-2H-naphtho[1,2-b]pyran-5-carboxylate (a) Ethyl 4-acetoxy-6-methoxy-2-naphthoate A solution of freshly distilled p-anisaldehyde (20 g, 146.9 mmol) and diethyl succinate (38.4 g, 220.3 mmol) in anhydrous ethanol (50 cm³) was added dropwise over 45 minutes to a vigorously stirred warm ~40–50° C., solution of sodium ethoxide (from sodium 6.75 g, 293.8 mmol) in anhydrous ethanol (450 cm³) under N$_2$. On completion of the addition the solution was refluxed for 4 hours and then cooled to room temperature.

The reaction mixture was reduced to ~⅕ of the original volume and the resulting viscous oil was diluted with water (700 cm³), cautiously acidified with c. HCl and the resulting two phase mixture extracted with ethyl acetate (5×100 cm³). The combined EtOAc solutions were extracted with aq. sat. NaHCO$_3$ solution (6×100 cm³). The combined aq. NaHCO$_3$ solutions were cautiously acidified with c. HCl and the resulting two phase mixture extracted with EtOAc (4×100 cm³). The combined EtOAc extracts were dried (Na$_2$SO$_4$) and evaporated to afford a yellow mobile oil.

A solution of the aforegoing yellow oil and anhydrous sodium acetate (12.05 g, 146.9 mmol) in acetic anhydride (180 cm³) was refluxed for 3 hours. The solution was cooled to room temperature and then diluted with water (2000 cm³) and allowed to stir for 1.5 hours. The resulting pale brown solid was collected by vacuum filtration, washed well with water (~500 cm³) and air dried.

The solid was recrystallised from EtOAc/hexane and Norit (activated charcoal) to give ethyl 4-acetoxy-6-methoxy-2-naphthoate (yield=21.2 g, theoretical yield= 42.35 g, 50%, m.p.=103.5–104.5° C. (uncorrected)).

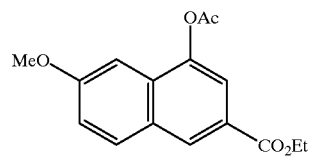

(b) Methyl 4-hydroxy-6-methoxy-2-naphthoate

A solution of ethyl 4-acetoxy6-methoxy-2-naphthoate (3.0 g, 10.4 mmol) and sodium hydroxide (2.5 g, 62.5 mmol) in water (60 cm³) and ethanol (15 cm³) was maintained at 80–90° C. for 3 hours. The cooled solution was poured into water (400 cm³) and cautiously acidified with c. HCl. The resulting suspension was extracted with EtOAc (5×75 cm³). The combined extracts were dried (Na$_2$SO$_4$) and evaporated to give a pale brown solid. This solid was dissolved in methanol (50 cm³) containing c. H$_2$SO$_4$ (~1 cm³) and was refluxed for 4 hours. The cooled mixture was diluted with water (500 cm³) and extracted with EtOAc (4×50 cm³). The combined extracts were washed with aq. sat. NaHCO$_3$ (2×100 cm³) and water (100 cm³). Removal of the dried (Na$_2$SO$_4$) EtOAc gave a pale brown solid which was recrystallised from EtOAc/hexane to afford methyl 4-hydroxy-6-methoxy-2-naphthoate (yield=1.63 g, theoretical yield=2.41 g, 68%, m.p.=193–195° C. (uncorrected)).

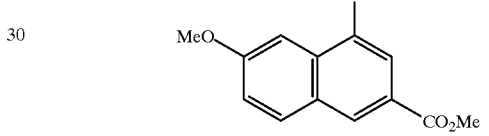

(c) Methyl 9-methoxy-2,2-bis(4-methoxyphenyl)-2H-naphtho [1,2-b]pyran-5-carboxylate.

A solution of methyl 4-hydroxy-6-methoxy-2-naphthoate (1.0 g, 4.3 mmol) and 1,1-di(4-methoxyphenyl)prop-2-yn-1-ol (1.16 g, 4.3 mmol) in toluene (45 cm³) containing acidic alumina (Brockmann 1), (4.0 g) was refluxed for 45 minutes. The cooled solution was filtered and the alumina was washed well with EtOAc (200 cm³). The organic filtrate was washed with aqueous sodium hydroxide (2M, 2×50 cm³) and water (100 cm³). Removal of the dried (Na$_2$SO$_4$) EtOAc gave an oil which was flash chromatographed over silica using 25% EtOAc in hexane as the eluent to afford a pale yellow solid. Recrystallisation from EtOAc/hexane gave methyl 9-methoxy-2,2-bis(4-methoxyphenyl)-2H-naphtho [1,2-b]pyran-5-carboxylate (yield=0.79 g, theoretical yield= 2.08 g 38%, m.p. 162.5–164.0° C. (uncorrected)).

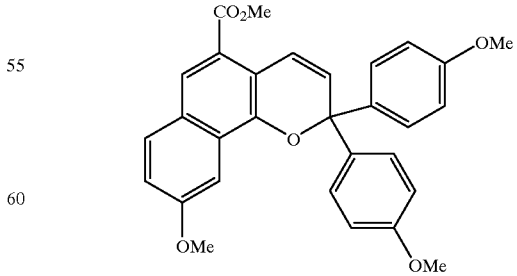

What is claimed is:
1. A polymeric host material including, or a solution of, a naphtho[1,2-b]pyran of general formula (I)

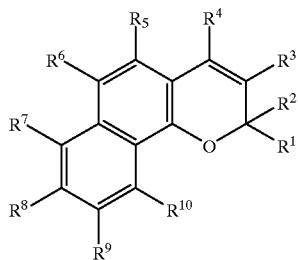

(I)

wherein $R^1$ and $R^2$ are each selected from unsubstituted, mono-, di- or polysubstituted aryl groups and heteroaryl groups, wherein each aryl group is not a naphthyl group;

$R^5$ is selected from linear or branched $C_1$–$C_{10}$ alkyl, $C_1$–$C_{20}$ cycloalkyl, $C_1$–$C_{20}$ bicycloalkyl, $C_1$–$C_{20}$ polycycloalkyl, linear or branched $C_1$–$C_{10}$ haloalkyl, linear or branched $C_1$–$C_{10}$ perhaloalkyl, linear or branched $C_1$–$C_{10}$ perhaloalkenyl, linear or branched $C_1$–$C_{10}$ alkenyl, $C_1$–$C_{10}$ alkynyl, linear or branched $C_1$–$C_{10}$ alkoxy, linear or branched $C_1$–$C_{10}$ alkylthio, linear or branched $C_1$–$C_{10}$ alkoxy, linear or branched $C_1$–$C_{10}$ hydroxyalkyl, linear or branched $C_1$–$C_{10}$ aminoalkyl, aryl, heteroaryl, halogen, nitrile, nitro, amino, linear or branched $C_1$–$C_{20}$ alkoxycarbonyl, hydroxyl, formyl, acetyl, amido, $C_1$–$C_5$ alkyl amido, $C_1$–$C_5$ dialkylamido, aroyl, benzoyl, alkyl $C_1$–$C_5$ amino, dialkyl $C_1$–$C_5$ amino, arylamino, diarylamino, aryl $C_1$–$C_5$ alkylamino and cyclicamino groups, arylsulfinyl, arylsulfanyl, arylsulfonyl, linear or branched $C_1$–$C_{10}$ alkylsulfonyl, P(O)(O—$C_1$–$C_{10}$ alkyl)$_2$ or is an alkenyl function of general formula:

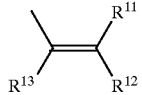

wherein $R^{11}$ and/or $R^{12}$ and/or $R^{13}$ is hydrogen or $R^5$, $R^3$, $R^4$, $R^6$, $R^8$ and $R^{10}$ are each hydrogen, $R^1$, $R^2$ or $R^5$, and $R^7$ and/or $R^9$ is hydrogen or an amino group provided that $R^7$ and $R^9$ are not both hydrogen.

2. A polymeric host material or a solution according to claim 1, wherein the amino group of $R^7$ and/or $R^9$ is selected from amino, linear or branched alkyl $C_1$–$C_{10}$ amino, linear or branched dialkyl $C_1$–$C_{10}$ amino, arylamino, diarylamino, linear or branched $C_1$–$C_{10}$ alkylamino and cyclicamino groups.

3. A polymeric host material or a solution according to claim 1, wherein the heteroaryl group of $R^1$ and $R^2$ is thienyl, benzo(b)thienyl, furyl, benzo(b)furyl, pyrryl, indolyl, pyrydyl, quinolyl, isoquinolyl, pyrimidyl, oxazolyl, isoxazolyl, thiazolyl, isothiazolyl, pyrazolyl, imidazolyl, benzimidazolyl, triazolyl, benzotriazolyl or tetrazolyl.

4. A polymeric host material or a solution according to claim 1, wherein the substituents for the aryl and heteroaryl groups representing $R^1$ and $R^2$ are linear or branched $C_1$–$C_{20}$ alkyl, $C_1$–$C_{20}$ cycloalkyl, $C_1$–$C_{20}$ bicycloalkyl, $C_1$–$C_{20}$ polycycloalkyl, linear or branched $C_1$–$C_{10}$ haloalkyl, linear or branched $C_1$–$C_{10}$ perhaloalkyl, linear or branched $C_1$–$C_{10}$ perhaloalkenyl, linear or branched $C_1$–$C_{10}$ alkenyl, $C_1$–$C_{10}$ alkynyl, linear or branched $C_1$–$C_{10}$ alkoxy, linear or branched $C_1$–$C_{10}$ alkylthio, linear or branched $C_1$–$C_{10}$ alkoxy (linear or branched $C_1$–$C_{10}$ alkyl), linear or branched $C_1$–$C_{10}$ hydroxyalkyl, linear or branched $C_1$–$C_{10}$ aminoalkyl, aryl, phenyl, heteroaryl, halogen, nitrile, nitro, amino, linear or branched $C_1$–$C_{20}$ alkoxycarbonyl, hydroxyl, formyl, acetyl, amido, $C_1$–$C_5$ alkyl amido, $C_1$–$C_5$ dialkylamido, aroyl, benzoyl, alkyl $C_1$–$C_5$ amino, dialkyl $C_1$–$C_5$ amino, arylamino, diarylamino, aryl $C_1$–$C_5$ alkylamino and cyclicamino groups arylsulfinyl, arylsulfanyl, arylsulfonyl, linear or branched $C_1$–$C_{10}$ alkylsulfonyl, P(O) (O—$C_1$–$C_{10}$ alkyl)$_2$.

5. A polymeric host material or a solution according to claim 1, wherein the cyclicamino group is aziridino, pyrrolidino, piperidino, morpholino, thiomorpholino, indolino, piperazino, $C_1$–$C_5$ N-Alkylpiperazino or N-arylpiperazino.

6. A polymeric host material or a solution according to claim 1, wherein $R^1$ and $R^2$ are each 4-methoxyphenyl, $R^5$ is methoxycarbonyl, and $R^9$ is morpholino, pyrrolidino or dimethylamino.

7. A polymeric host material according to claim 1, wherein the material is a plastic or a glass.

8. A window, an optical filter, an ophthalmic lens or a sunglass lens made from a polymeric host material according to claim 1.

9. The polymeric host material of claim 1, wherein $R^1$ and $R^2$ are each selected from 10. The polymeric host material of claim 1, wherein $R^5$ is phenyl.

* * * * *